United States Patent [19]

Nelson et al.

[11] Patent Number: 4,847,198
[45] Date of Patent: Jul. 11, 1989

[54] DETECTION AND INDENTIFICATION OF BACTERIA BY MEANS OF ULTRA-VIOLET EXCITED RESONANCE RAMAN SPECTRA

[75] Inventors: Wilfred H. Nelson; Richard A. Dalterio, both of Kingston; Jay F. Sperry, Peacedale, all of R.I.

[73] Assignee: The Board of Governors for Higher Education, State of Rhode Island and Providence Plantations, Providence, R.I.

[21] Appl. No.: 916,214

[22] Filed: Oct. 7, 1987

[51] Int. Cl.[4] .................. C12Q 1/04; C12N 13/00; G01J 3/44
[52] U.S. Cl. .................................... 435/34; 356/301; 435/29; 435/173; 435/808; 436/63
[58] Field of Search ................ 356/301; 435/29, 34, 435/173, 808; 436/63

[56] References Cited

U.S. PATENT DOCUMENTS 4,411,525  10/1983  Ogawa ........................... 356/318 X
4,505,586   3/1985  Tuchigi et al. .................... 356/301
4,678,277   7/1987  Delhaye et al. ................... 356/301

OTHER PUBLICATIONS

Chemical Abstracts 92, (1980), p. 278, Abst. #185583h, Howard W. F., Jr. et al., "A Resonance Raman Method . . .".
Chemical Abstracts 104, (1986), p. 353, Abst. #105425m, Dalterio R. A. et al., "A Resonance Raman Microprobe Study . . .".

Primary Examiner—Robert J. Warden
Assistant Examiner—Richard W. Wagner
Attorney, Agent, or Firm—Samuels, Gauthier Stevens & Kehoe

[57] ABSTRACT

A bacterial suspension is contacted by a single vavelength in the ultra-violet range. A portion of the light energy used is absorbed and a portion of the light energy is emitted. The emitted light energy, resonance enhanced Raman scattering, is measured as backscattered energy. The energy is processed to produce spectra which are characteristic of the bacteria.

5 Claims, 8 Drawing Sheets

DETECTION AND INDENTIFICATION OF BACTERIA BY MEANS OF ULTRA-VIOLET EXCITED RESONANCE RAMAN SPECTRA

BACKGROUND AND BRIEF SUMMARY OF THE INVENTION

Presently, many effective methods for the identification of microorganisms are available. These methods vary widely in sensitivity and specificity. Most commonly, cultural examinations of bacteria are made which require much time and often are not specific unless extremely tedious procedures are followed. The lack of speed characteristic of many routine analyses is a serious problem. Frequently, important decisions relating to the presence of pathogens have to be made before the results of microbiological tests are available, because present methods of detection and identification are, in many cases, too slow or nonspecific to be of much immediate help to decision-makers or potential victims.

The last quarter century, and especially the last decade, has seen a revolution in the application of sensitive and rapid methods of chemical analysis. This has happened, to a large extent, due to advances in electronics, optics, and computer technology which have allowed the practical application of physical methods which previously had been understood in theory, but were too cumbersome to use. These methods have had a major impact on analytical laboratories by making previously difficult analyses affordable and routine and by providing many opportunities for automation.

However, until relatively recently, there was little promise of applying these sophisticated new techniques to biodetection because of the lack of information regarding the molecular composition of microorganisms. Today, chemical information can be used effectively to establish relationships at all levels in the taxonomic hierarchy. Chemical properties, it appears, can and must be used in description of many genera and species.

The progress of biochemists and microbiologists in characterizing and identifying chemical markers has not gone unnoticed by chemical analysts. During the past several years, there has been marked progress in methods of chemical analysis and automation in biodetection and identification. Several potentially rapid new physical methods have been developed in the past several years which promise to achieve truly rapid analysis.

Among the most highly developed of the new rapid techniques is mass spectroscopy and its various combinations with gas chromatography (bacterial biproducts from cultures) and pyrolysis methods. Gas chromatography is highly effective in detecting characteristic bacterial metabolic products. Flow cytometry has provided means for the rapid detection, identification, and separation of cells. Total luminescence spectroscopy can detect organisms very rapidly. The various immunological methods also can be very specific and very rapid. All of these methods have their distinct advantages and disadvantages.

Mass spectroscopy may be unequalled in identification of pure cultures, and it is very rapid and sensitive. However, it is expensive to use, requires the destruction of samples, and is of questionable use in the analysis of complex mixtures. Flow cytometry is perhaps even more costly, requires extensive sample preparation, and in many aspects is limited in its scope of applicability. Luminescence techniques are of little use except in studies of pure cultures unless combined with immunological methods. Immunological methods are unequalled in specificity and speed, as well as sensitivity. Yet, they are often impractical to use unless very expensive and perishable materials are available in a state of constant readiness. Such methods are not practical for a wide range of organisms. Gas chromatography requires that cells be grown and, hence, this method is generally slow and of limited applicability.

The present invention is directed to a new method, and a system embodying that method, for the rapid detection and identification of bacteria and other microorganisms. The invention broadly includes a method wherein a beam of visible or ultraviolet light energy contacts a microorganism under investigation. A portion of the light energy is absorbed by the microorganism and a portion of the light energy is 'emitted' from the sample at a lower energy level. The emitted light energy (resonance enhanced Raman scattering) may be measured at any angle but preferably is measured as backscattered energy. This energy is processed to produce spectra which are inherently characteristic of the microorganism.

The light energy which contacts the microorganism may be at any wavelenth so long as it corresponds to a molecular electronic transition which corresponds to strong absorption by the organism. Preferably the energy is a single selected wavelength in the ultraviolet range since most electronic transitions of component molecules of microorganisms occur in that range.

In a preferred embodiment, the emitted energy measured is based upon ultraviolet resonance Raman spectroscopy. Bacteria under investigation are struck by an incident beam of light energy, typically a single wavelength in the ultraviolet range. The emitted energy is collected, collimated and focused onto the entrance slit of a monochromator. The beam strikes a grating or gratings and the wavelengths reflected by the grating or gratings are plotted versus intensity to obtain a spectrum. The chemotaxonomic markers inherent in the bacteria are different for each bacterial type and these differences are reflected in the distinct spectra generated. With a known sample the characteristic spectra are plotted and these spectra, which are stored, are the 'fingerprints' of that bacterium. When unknown samples are analyzed, their spectra are compared with the known spectra in memory to determine the identity of the unknown sample.

DESCRIPTION OF THE PREFERRED EMBODIMENT(S)

Figure 1:
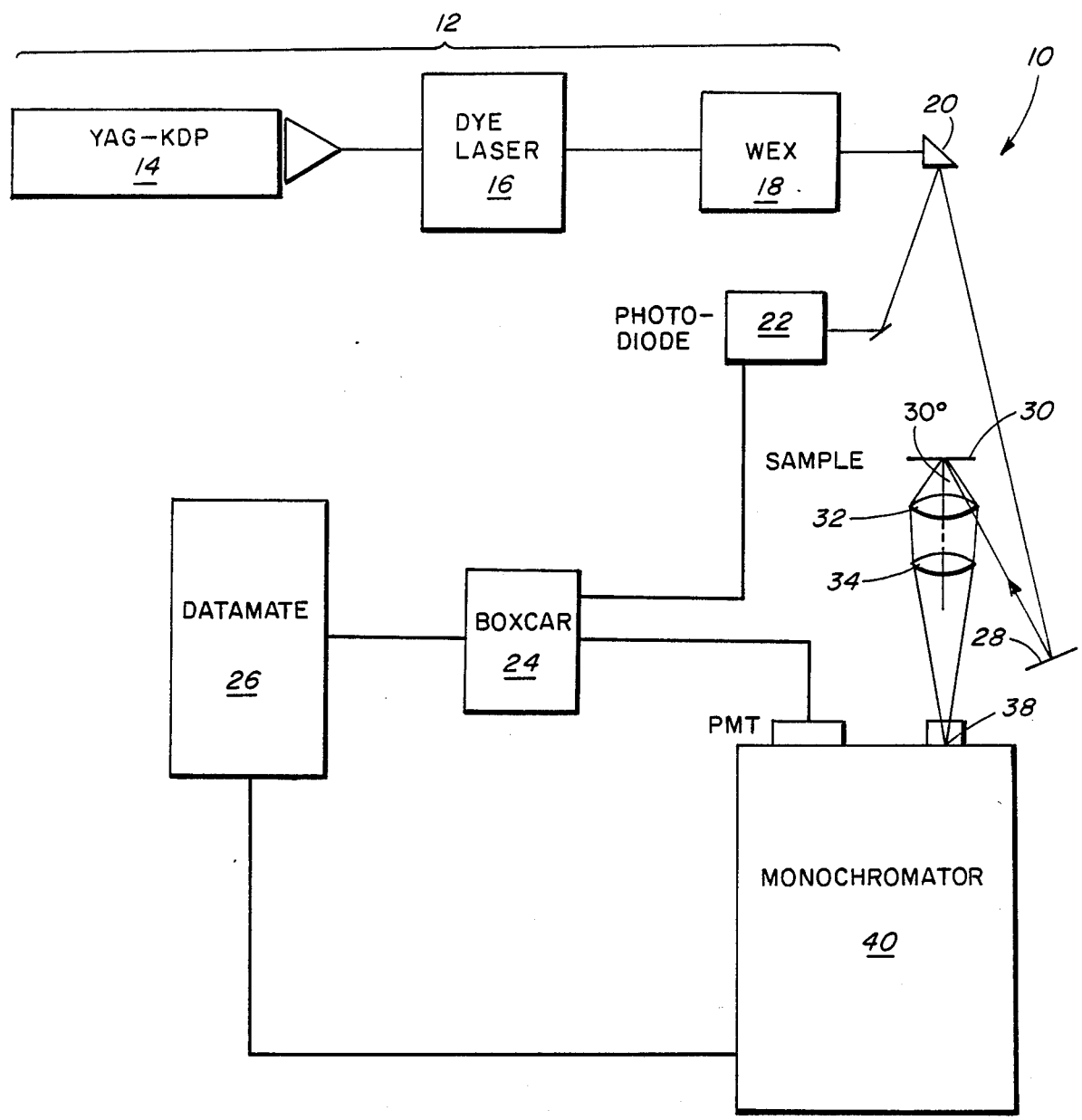
FIG. 1 is a schematic representation of a system embodying the invention.

A schematic representation of a system 10 embodying the invention is shown in FIG. 1. A light source 12 comprises three major components: a Nd-Yag (Quanta-Ray DCR-1A) laser 14 which produces high energy light pulses at 1064 nm, 532 nm, 355 nm, and 266 nm, a dye laser 16 (Quanta-Ray PDL-2) which shifts pulse energies from Yag frequencies to lower energies, and a wavelength extender 18 (WEX: Quanta Ray) which either doubles the dye laser output or mixes the dye-laser output or doubled dye laser output with an Nd-Yag fundamental to produce pulsed UV light at a wavelength between 350–216 nm. The output from the wavelength extender 18 strikes a split prism 20 which produces two beams. A first reference beam strikes a mirror 5 and is reflected onto a photodiode 22. The output from the photodiode is transmitted to a Princeton Applied Research Model 162 Boxcar Averager 24. A Spex Datamate DMO1 microcomputer 26 controls the stepping motor (not shown) of a monochromator 40, general data acquisition and disc storage of spectra.

The second beam from the prism 20 strikes a mirror 28 which directs the beam to a sample 30 under investigation. The energy backscattered from the sample is collimated by a lens 32, condensed by an optically aligned lens 34 and focused by the lens 34 on an entrance slit 38 of the monochromator 40.

The formation of a single wavelength in the ultraviolet range, the use of that wavelength to create spectral information about a specimen and the control and output of that information in various graphic or tabular forms is within the scope of those skilled in the art. Where the present invention primarily differs from prior art techniques is in the collection and use of backscattered energy i.e., resonance enhanced Raman scattering from a microorganism which exhibits characterstic spectra of that microorganism. The spectra observed reflect the differences in the composition among the organisms which allow the organisms to be readily identified. The invention will be described with particular reference to the following Example, which Example is illustrative of and not a limitation of the scope of the invention.

EXAMPLE

The laser 14 contained an angle tuned crystal harmonic generator which doubled a 1064 nm Yag output to 532 nm. This 532 nm output was used to pump the dye laser 16 which, in turn, emitted a beam at 627.8 nm. The extender 18 then frequency doubled the dye laser output and mixed it with the Yag 1064 nm fundamental to obtain the 2424.0 A output used.

The monochromator 40 was a Spex Model 1702:0.75 meter single grating unit with wavelength drive. A 3600 line/mm grating was employed in the first order for maximum UV grating efficiency. Entrance and exit slits were set at 200 um for all spectra. The detector used was a Hamamatsu R166UH high gain "solar blind" tube which is insensitive to wavelengths longer than 320 nm. Cathode voltage was 900 v. Use of the "solar blind" tube minimized stray light interference originating from fluorescing biological samples. The Spex Datamate microcomputer 26 controlled the stepping motor of the monochromator and general data acquisition.

The Boxcar Averager 24 was combined with two Model 166 Gated Integrators (not shown) and used for signal recovery. The photodiode 22 monitored the double dye laser output and was used to trigger the averager as well as to provide a signal proportional to the laser power for use in signal ratioing against the PMT signal channel to compensate for pulse-to-pulse laser intensity variations. A 15 ns aperature duration was used to capture the PMT signal and a 100 s time constant was used in each gated integrator. Scan speeds of 12s/0.2 A and 10s/0.1 A were used resulting in scan times of 53 and 88 minutes, respectively, for 900–1750 $cm^{-1}$ scans. The wavelength calibration was by means of standard mercury lines.

The sample cell 30 was a 2-inch length cell of 4 mm o.d., 3 mm i.d. suprasil quartz tubing. The samples were continuously recirculated with a Masterflex tubing pump (Cole Parmer Instrument Co.). A flow rate of 15 ml/minute was used for sample volumes of 10 ml for chemicals and 4 ml for bacterial suspensions.

Spectra of chemical samples i.e., nucleotides, tyrosine, and trypyophan (1 millimole per liter-aqueous solution) were obtained to determine the likely origin of the bacterial spectral components.

All test samples were composed of suspensions of bacterial cultures. Specifically, the bacterial suspensions were formed as follows *Staphylococcus epidermidis* ATCC 12228; *Enterobacter cloacae* ATCC 23355 and *Escherichai coli* ATCC 25922 were obtained from the American Type Culture Collection, Rockvile, MD. *Pseudomonas fluorescens* #63 was obtained from the Midwest Culture Service, Terre Haute, Ind., *Bacillus subtilis* was obtained from the Microbiology Department, Univeristy of Rhode Island, Kingston, R.I. Stock cultures were maintained at 4° C. following incubation at the proper growth temperatures for 24 hours. Experimental samples were obtained by inoculating a nutrient agar slant with bacteria and incubating the culture for 24 hours. *B subtilis* and *P. fluorescens were incubated at* 30° C. The bacteria were then washed from the nutrient slants with 4–5 ml of sterile 0.85% saline. The bacterial density after dilution was approximately $10^8$–$10^9$ organisms/ ml. The excitation beam from the extender 18 was focused onto the sample cell 30 with a 10 cm focal length lens 28 placed 8.3 cm from the sample cell. To minimize the effect of sample optical density on the scattered light intensity, 30° back-scattering geometry was used. The scattered light was collected with a 2-inch diameter 6.5 cm focal length quartz lens 32 and focused onto the entrance slit 38 of the monochromator with a 35.0 cm focal length quartz lens 34. Because of the highly scattering nature of the bacterial samples, a filter was devised to exclude Rayleigh scattering. For this purpose a 0.7 mM solution of quinoline in 1.0 M HCl was placed in a 1 cm path length cuvette in front of the entrance slit. The quinoline efficiently absorbs 2424 A light while transmitting 40–50% of light in the range 247–260 nm (The Raman range). The average laser beam power at the sample was 6–7 mW. (A second monochromator would serve to exclude Rayleigh scattered light more efficiently).

Figure 5:
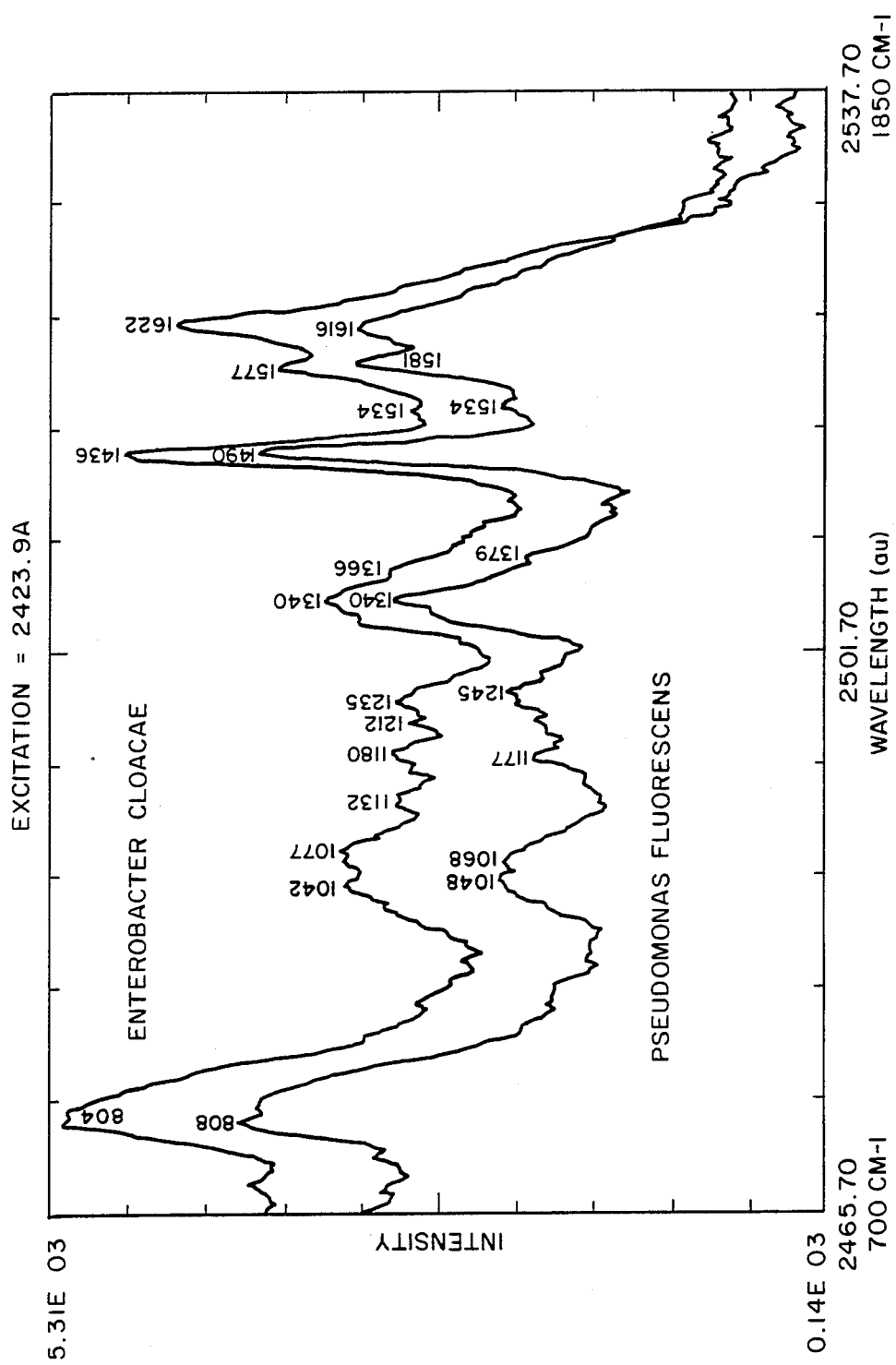
Figure 6:
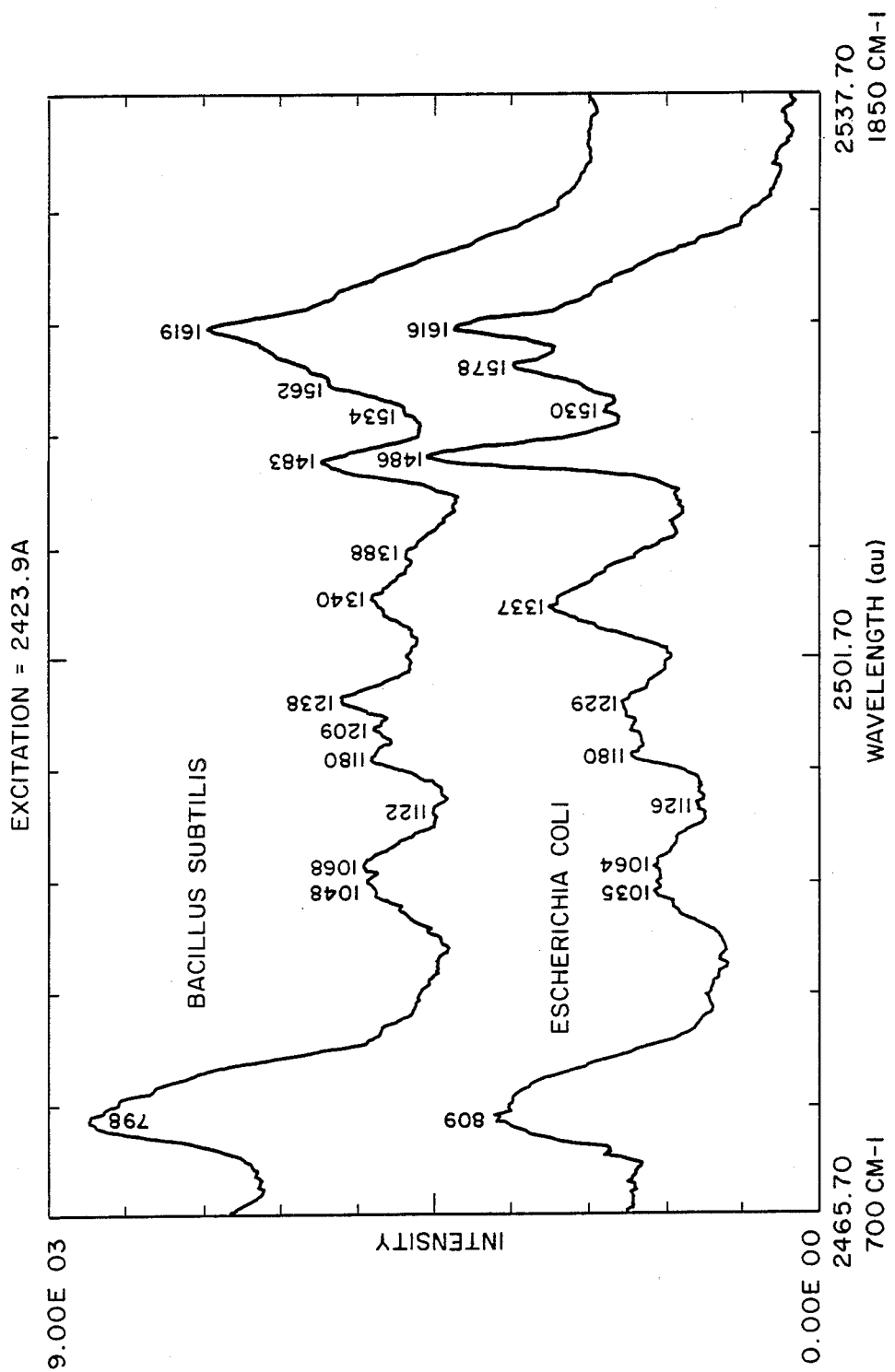
Figure 7:
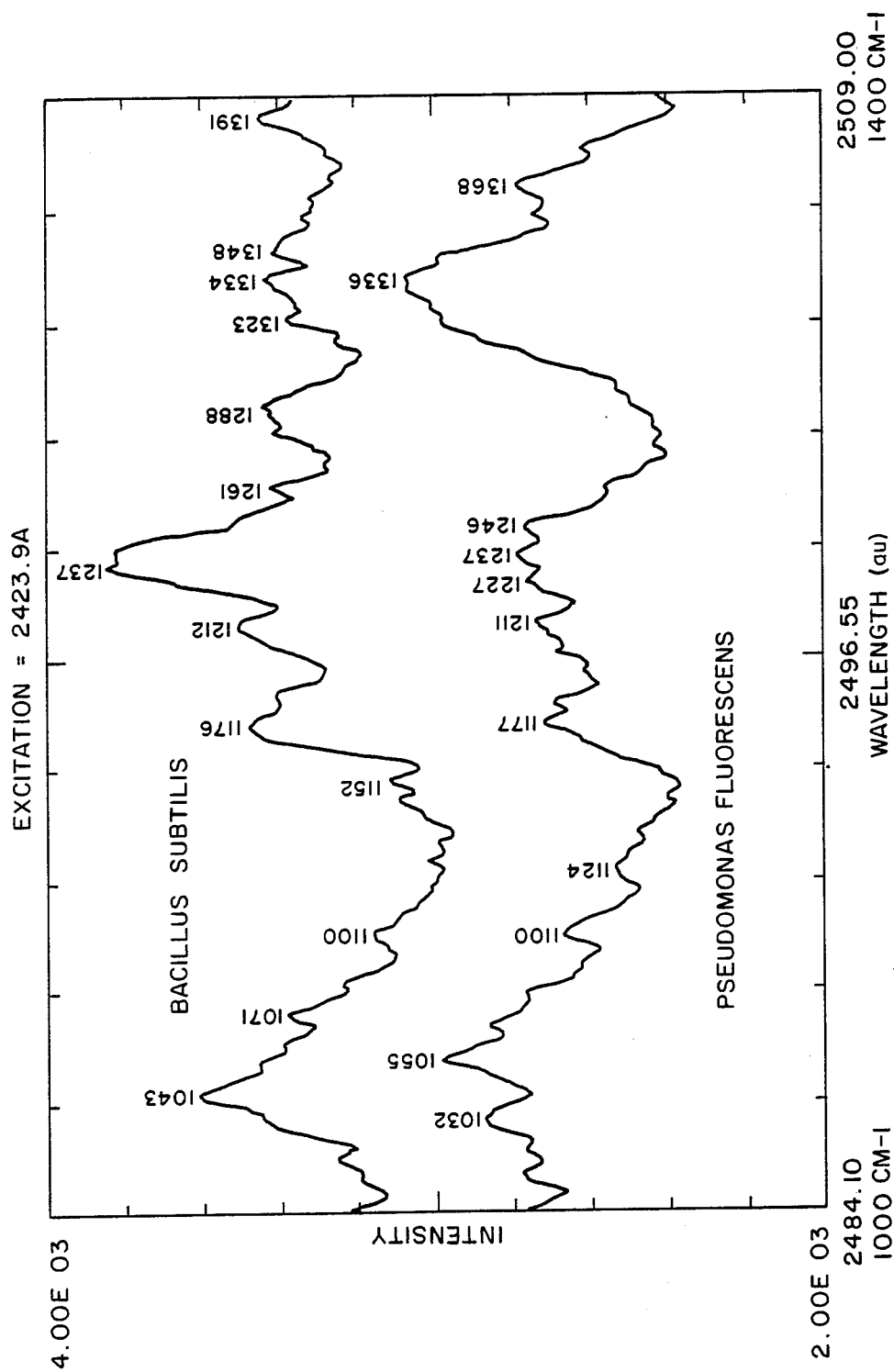
Figure 8:
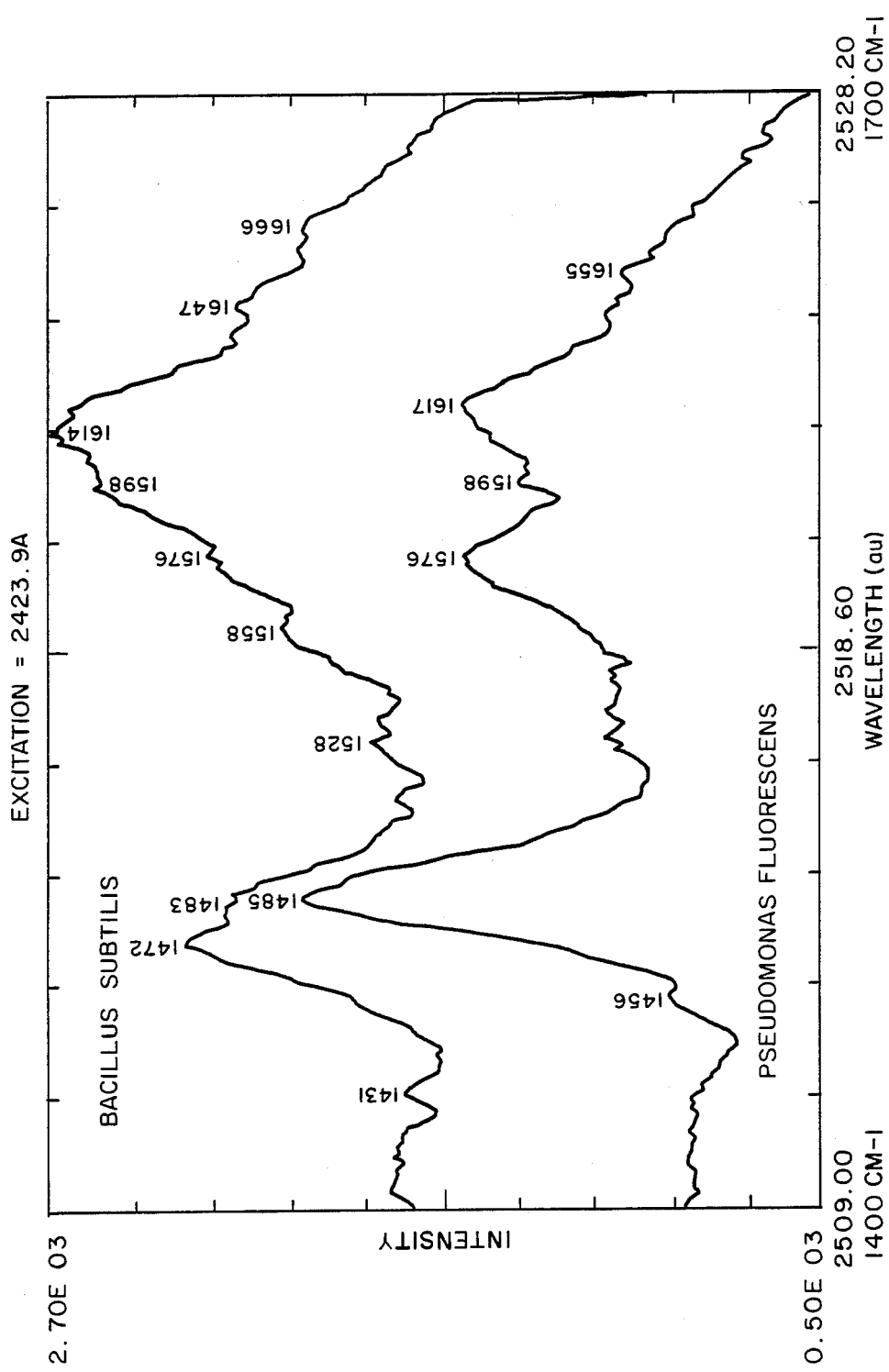

The spectra shown in FIGS. 2–8 were taken using a single wavelength of 242 nm. The bacteria investigated are identified in the Figures. FIGS. 2–6 are low resolution spectra while FIGS. 7–8 are higher resolution spectra.

Figure 2:
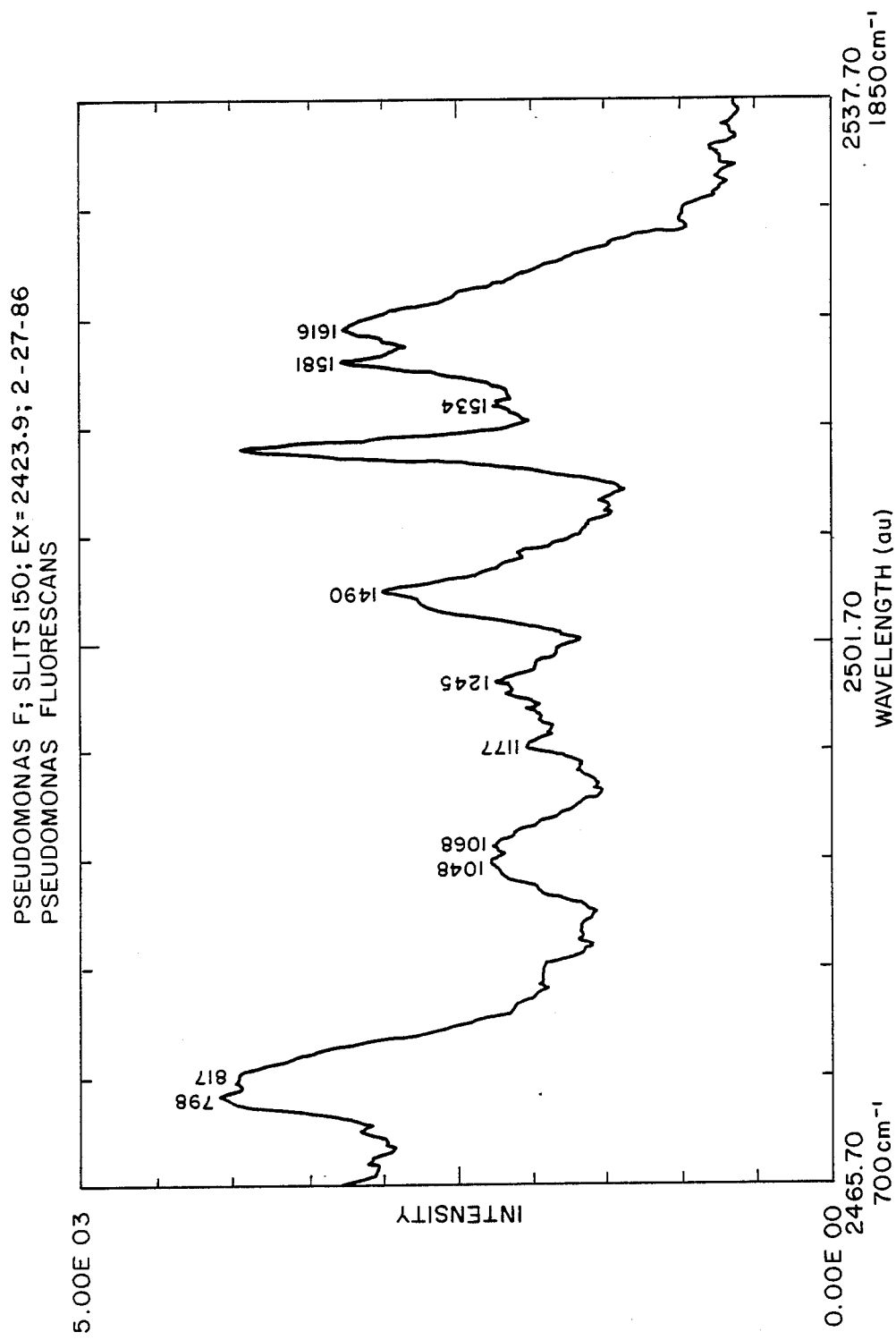
FIGS. 2–8 are graphical representations of the spectral characteristics of different bacteria generated in accordance with our invention.

FIG. 2 shows a single low-resolution spectrum of *Pseudomonas fluorescens* (#63) taken in a 70-minute scan. The spectra of FIGS. 3–8 are averages of three scans.

Figure 3:
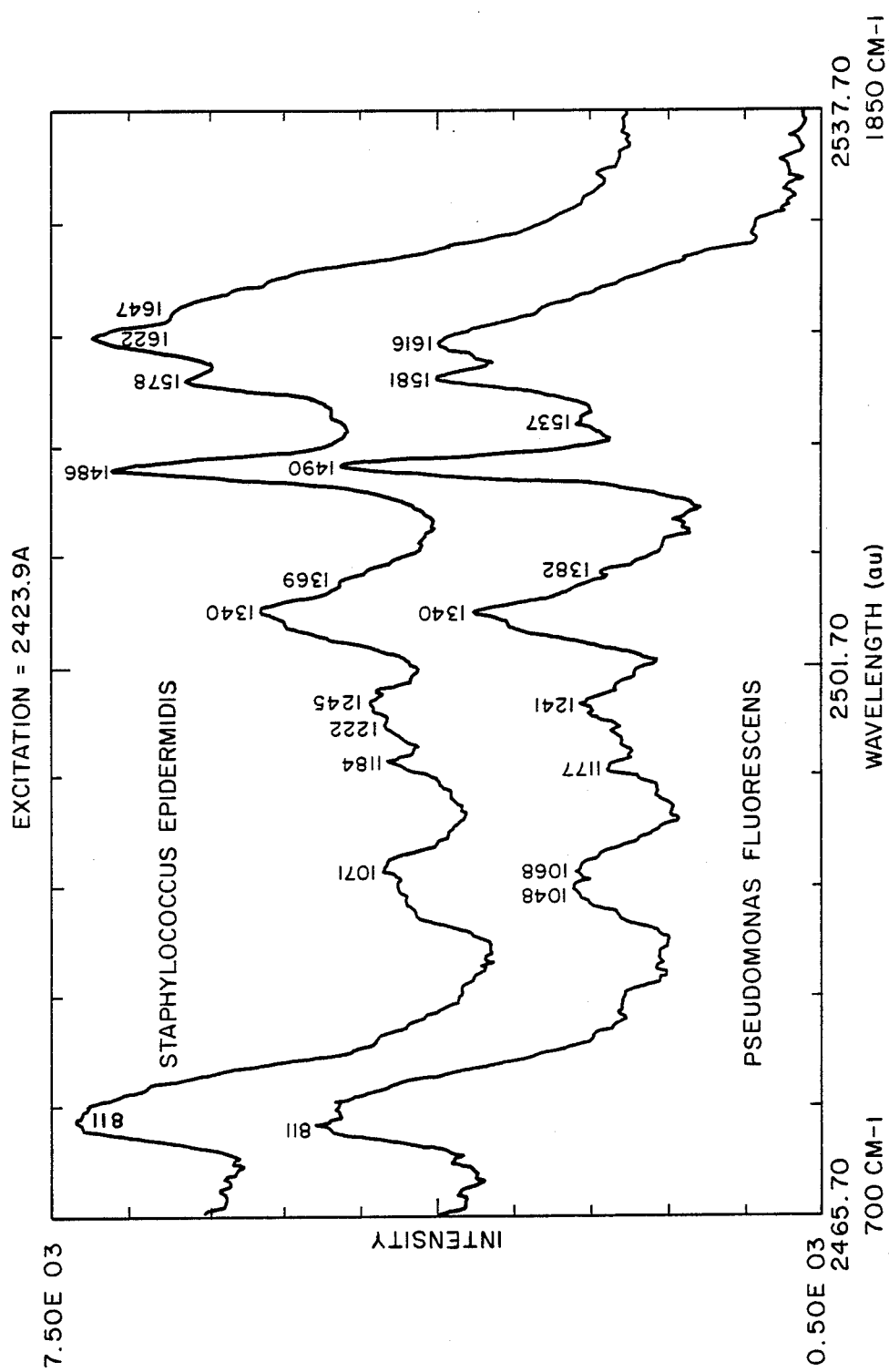
Figure 4:
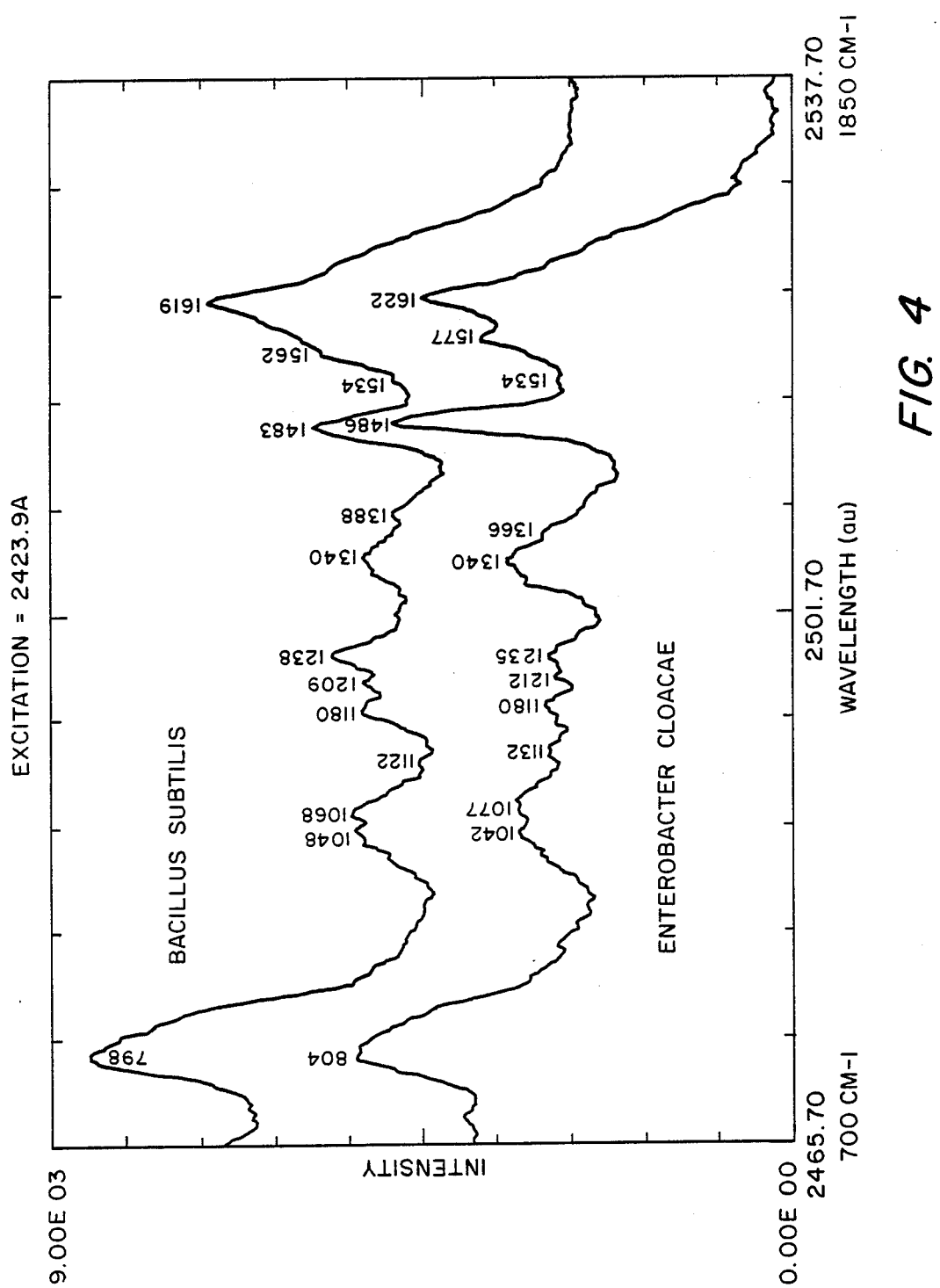

Referring to FIGS. 3, 4 and 6 comparisons of spectra belonging to Gram-negative and Gram-positive organisms are especially clear-cut. The peaks near 1600 $cm^{-1}$ (probably associated with protein) show this most clearly.

As shown in FIG. 5, comparisons between spectra of organisms of the same Gram stain type show fewer spectral differences but the differences in peak positions and relative peak heights are still very marked.

FIGS. 7 and 8 compare spectra of *Bacillus subtilis* (URI collection) and *Pseudomonas fluorescens* (#63) over shorter spectral ranges. This allows the full resolution of the data to be observed directly. The differences shown in FIG. 8 are especially significant and marked.

In all cases background due to contributions other than resonance Raman scattering was very low. The rise in the baseline approaching 700 cm$^{-1}$ is due to small amounts of Rayleigh scattering.

It is believed the spectra strongly support our claim that bacteria and other microorganisms can be rapidly detected and identified by means of UV-excited resonance Raman spectroscopy.

The spectra of organisms studied at the genus level reflected major differences in numbers and types of chemotaxonomic markers. In the example our method and system was effective using 190–260 nm laser excitation due to the absence of fluorescence when those wavelengths are used. Different exciting laser wavelengths will selectively excite different sets of taxonomic markers, giving rise to distinct spectral fingerprints at each wavelength, further enhancing the effectiveness of the method and system.

We have shown that with the five different types of bacteria excited at 242 nm at a power of about 5 mw characteristic resonance Raman spectra are exhibited which sensitively reflect differences in the compositions of these organisms. Nucleic acids, proteins and possibly isoprenoid quinones and other marker components are major contributors to the spectra reported. Fluorescence produced at energies below 270 nm by the organisms and associated media does not interfere with the resonance Raman signals since a "window" between the exciting frequency and the onset of fluorescence allows the sensitive detection of resonance-enhanced Raman scattered light. The higher the energy of the excited light within the Raman window (190–270 nm) the larger the "Raman window."

Based on the Example, major spectral differences have been observed associated with the five types of organisms studied. The data have been reproduced at least three times for each culture studied. Each organism has been cultured repeatedly and the spectra obtained. In all cases, spectra are highly reproducible except in the case of *Bacillus subtilis* which showed substantial differences attributable to endospore formation. The broad peaks centered near 800cm$^{-1}$ and 1060 cm$^{-1}$ are due primarly to the quartz cell and can be used as an internal standard.

It is believed that spectral differences will be observed at other wavelengths.

From known absorption characteristics of chemotaxonomic markers and the results shown in FIGS. 2–8, it is believed that at wavelengths between 190–260 nm characteristic resonance Raman spectra of bacteria and other microorganisms can be obtained. Depending upon chemotaxonomic relationships, different organisms, including pathogens i.e., disease causing microorganisms, will give characteristic spectra at empirically chosen excitation wavelengths between 190–260 nm. Spectra will reflect chemotaxonomic differences and will vary in the number, intensity, and energy of peaks. Single cell detection should be possible if a microscope-equipped system is used with a CW or a low power pulsed source which will not damage the samples. Truly rapid analysis should be possible if an optical multichannel analyzer is used for detection rather than the present scanning system. It is anticipated that a library of spectra will be obtained and placed in storage such as on disc which can be rapidly scanned by a computer allowing rapid identification on the basis of resonance Raman spectra.

Because existing laser wavelengths can be varied and because single cell detection can be predicted, direct detection from gross mixtures should be possible. Because all microorganisms, including viruses, possess chemotaxonomic markers which absorb in the ultraviolet, this method should work for all microorganisms.

Our invention has been described with reference to a specific geometric configuration for the collection of backscattered energy. It is within the scope of this invention that backscattered energy may be collected by any suitable technique within an angular range from 0° to 90° and preferably within a range of from 0° to 45° with the angular relationship being defined as the angle between the incident beam and the axis along which the backscattered energy is collected.

The generation of the characteristic spectra was described in reference to a mechanically driven eschelle grating. Other techniques which would be suitable for purposes of the invention to ultimately display the unique spectra associated with the microorganism under examination include the combination of a spectrograph and a multichannel analyzer. It would be possible in principal to use photographic detection as well.

In the preferred embodiment specific bacteria were described. It is believed that any of the microorganisms can be so identified. For the purposes of this disclosure the term 'microorganism' includes bacteria, viruses (including the AIDS virus), fungi, algae and protozoa or protista such as set forth in "Microbiology" Third Edition, B. D. Davis, R. Dulbecco, H. N. Eisen and H. S. Ginsberg, Harper and Row Publishers, Philadelphia (1980), which publication is hereby incorporated by reference in its entirety into this disclosure.

In the Example, the test samples were suspensions of bacterial cultures. The microorganisms may be embodied in any biologically acceptable carrier or medium wherein the sample microorganisms will emit energy which will produce spectra characteristic of the microorganism.

Having described our invention, what we now claim is:

1. A method for the identification of a bacterium which comprises:
   exciting taxonomic markers in a bacterium with a beam of ultra violet energy, some of said energy emitted from the bacterium as a lower resonance enhanced Raman back scattered energy;
   collecting the resonance enhance Raman back scattered energy substantially in the absence of fluorescence;
   converting the resonance enhanced Raman back scattered energy into spectra which corresponds to the taxonomic markers in said bacterium; and
   displaying the spectra whereby the bacterium may be identified.

2. The method of claim 1 wherein the beam of energy is in the wavelength range of 190 to 270 nm.

3. The method of claim 1 wherein the back scattered energy is collected at an angle of between 0° to 90° based on the angle between the beam of energy and the axis along which the back scattered energy is collected.

4. The method of claim 1 wherein the displaying of the spectra includes:
   plotting the spectral lines.

5. The method of claim 1 which includes:
   plotting the spectral lines as a function of wavelength.

* * * * *